(12) United States Patent
Huschke (10) Patent No.: US 10,309,556 B2
(45) Date of Patent: Jun. 4, 2019

(54) STERILE PORT CONNECTION

(71) Applicant: SAINT-GOBAIN PERFORMANCE PLASTICS CORPORATION, Solon, OH (US)

(72) Inventor: Michael R. Huschke, Midland, MI (US)

(73) Assignee: SAINT-GOBAIN PERFORMANCE PLASTICS CORPORATION, Solon, OH (US)

( * ) Notice: Subject to any disclaimer, the term of this patent is extended or adjusted under 35 U.S.C. 154(b) by 460 days.

(21) Appl. No.: 15/085,549

(22) Filed: Mar. 30, 2016

(65) Prior Publication Data

US 2016/0305577 A1 Oct. 20, 2016

Related U.S. Application Data (60) Provisional application No. 62/149,162, filed on Apr. 17, 2015.

(51) Int. Cl.
| | |
|---|---|
| *F16L 5/00* | (2006.01) |
| *A61M 39/12* | (2006.01) |
| *A61M 39/16* | (2006.01) |
| *A61M 39/18* | (2006.01) |
| *A61M 39/08* | (2006.01) |

(52) U.S. Cl.
CPC ............... *F16L 5/00* (2013.01); *A61M 39/12* (2013.01); *A61M 39/16* (2013.01); *A61M 39/18* (2013.01); *A61M 2039/087* (2013.01)

(58) Field of Classification Search
CPC ..... F16L 5/02; F16L 5/00; F16L 5/027; F16L 5/10; A61M 39/12

USPC ...... 285/141.1, 139.2, 139.3, 215, 217, 242, 285/250
See application file for complete search history.

(56) References Cited

U.S. PATENT DOCUMENTS

| | | | |
|---|---|---|---|
| 2,127,903 A | 8/1938 | Bowen | |
| 2,868,564 A * | 1/1959 | Arras | F16L 33/225 285/243 |
| 3,076,668 A * | 2/1963 | Famely | F16L 5/027 248/56 |
| 3,423,518 A * | 1/1969 | Weagant | H02G 3/0675 285/140.1 |
| 3,458,619 A | 7/1969 | Prochaska | |
| 3,463,691 A | 8/1969 | Martin | |

(Continued)

FOREIGN PATENT DOCUMENTS

| | | | |
|---|---|---|---|
| CA | 580160 A | 7/1959 | |
| DE | 4109206 C1 * | 5/1992 | F16L 5/027 |

(Continued)

OTHER PUBLICATIONS

International Search Report and Written Opinion for PCT/US2016/025018, dated Jul. 6, 2016, 11 pages.

(Continued)

*Primary Examiner* — David Bochna
(74) *Attorney, Agent, or Firm* — Abel Law Group, LLP; Chi Suk Kim (57) ABSTRACT

Embodiments of the present disclosure are directed to connection assemblies providing a connection between a tubing and a port. The port can be disposed within and particularly extending through a bore of the port. The port and tube are coupled to provide an aseptic connection.

17 Claims, 7 Drawing Sheets

(56) References Cited

U.S. PATENT DOCUMENTS

| | | | |
|---|---|---|---|
| 3,540,223 A | 11/1970 | Ebbe | |
| 4,070,044 A | 1/1978 | Carrow | |
| 4,076,282 A | 2/1978 | Scott, Jr. et al. | |
| 4,161,949 A | 7/1979 | Thanawalla | |
| 4,203,436 A | 5/1980 | Grimsrud | |
| 4,321,911 A * | 3/1982 | Offutt | F24S 80/30 |
| | | | 285/242 |
| 4,596,557 A | 6/1986 | Pexa | |
| 4,621,937 A * | 11/1986 | Maccuaig | F16L 5/02 |
| | | | 285/192 |
| 4,661,110 A | 4/1987 | Fortier et al. | |
| 4,795,465 A | 1/1989 | Marten | |
| 4,815,769 A | 3/1989 | Hopperdietzel | |
| 4,997,213 A | 3/1991 | Traner et al. | |
| 5,254,097 A | 10/1993 | Schock et al. | |
| 5,292,305 A | 3/1994 | Boudewijn et al. | |
| 5,295,760 A * | 3/1994 | Rowe | B67D 7/3209 |
| | | | 285/192 |
| 5,335,944 A | 8/1994 | Mitsui et al. | |
| 5,411,300 A | 5/1995 | Mitsui | |
| 5,429,397 A | 7/1995 | Kanao | |
| 5,447,341 A | 9/1995 | Härtel et al. | |
| 5,453,088 A | 9/1995 | Boudewijn et al. | |
| 5,568,949 A | 10/1996 | Andre | |
| 5,573,527 A | 11/1996 | MacAbasco et al. | |
| 5,704,656 A * | 1/1998 | Rowe | F16L 5/02 |
| | | | 285/139.3 |
| 5,864,938 A | 2/1999 | Gansel et al. | |
| 5,945,052 A | 8/1999 | Schryver et al. | |
| 6,123,365 A * | 9/2000 | Lambing | F16L 5/10 |
| | | | 285/139.2 |
| 6,290,265 B1 | 9/2001 | Warburton-Pitt et al. | |
| 6,432,345 B1 | 8/2002 | Warburton-Pitt | |
| 6,485,479 B1 | 11/2002 | Knierbein | |
| 6,635,214 B2 | 10/2003 | Rapacki et al. | |
| 6,910,870 B2 * | 6/2005 | Ebner | F04D 13/10 |
| | | | 166/65.1 |
| 7,026,549 B1 * | 4/2006 | Smutny | F16L 5/027 |
| | | | 248/56 |
| 7,093,859 B2 | 8/2006 | Warburton-Pitt et al. | |
| 7,407,612 B2 | 8/2008 | Warburton-Pitt et al. | |
| 7,758,084 B2 * | 7/2010 | Boudry | F16L 5/022 |
| | | | 285/139.2 |
| 7,758,086 B2 | 7/2010 | Slunick et al. | |
| 7,922,212 B2 | 4/2011 | Werth | |
| 7,922,213 B2 | 4/2011 | Werth | |
| 8,256,802 B2 | 9/2012 | Werth | |
| 8,656,553 B2 * | 2/2014 | Okuhara | B60R 16/0222 |
| | | | 16/2.1 |
| 8,662,542 B2 | 3/2014 | Werth | |
| 9,920,859 B2 * | 3/2018 | Perrigo | F16L 5/00 |
| 2002/0050663 A1 | 5/2002 | Warburton-Pitt et al. | |
| 2004/0189004 A1 * | 9/2004 | Wright | F16L 5/02 |
| | | | 285/189 |
| 2005/0012332 A1 * | 1/2005 | Werth | A61M 39/12 |
| | | | 285/322 |
| 2005/0082826 A1 | 4/2005 | Werth | |
| 2008/0267699 A1 | 10/2008 | Warburton-Pitt et al. | |
| 2009/0136286 A1 * | 5/2009 | Kenney | F16L 5/02 |
| | | | 403/51 |
| 2009/0199927 A1 * | 8/2009 | Kane | F16L 5/10 |
| | | | 285/141.1 |
| 2009/0232586 A1 | 9/2009 | Diodati et al. | |
| 2012/0223517 A1 | 9/2012 | Morrissey et al. | |
| 2012/0296314 A1 | 11/2012 | Reavill | |
| 2013/0025107 A1 * | 1/2013 | Higgins | F16L 5/025 |
| | | | 285/141.1 |
| 2013/0043676 A1 | 2/2013 | Baker | |
| 2014/0077461 A1 * | 3/2014 | Warren | F16L 5/10 |
| | | | 277/606 |
| 2014/0091569 A1 | 4/2014 | Spohn et al. | |
| 2015/0108080 A1 * | 4/2015 | Grittmann | B65D 39/12 |
| | | | 215/359 |
| 2016/0356403 A1 * | 12/2016 | Perrigo | F16L 5/00 |

FOREIGN PATENT DOCUMENTS

| | | | | |
|---|---|---|---|---|
| JP | H0642687 A | 2/1994 | | |
| JP | H06101791 A | 4/1994 | | |
| JP | H06101792 A | 4/1994 | | |
| WO | WO-2012124203 A1 * | 9/2012 | | B60R 16/0222 |
| WO | 2016167966 A1 | 10/2016 | | |

OTHER PUBLICATIONS

Sani-Tech Products, "More premium-quality products for R&D, process development, scale-up and production," 1996, 2 pages, Nalge Process Technologies Group, Lafayette, US.

Top Works, "Sealing and Fluid Transfer Systems," 14 pages, Nalge Process Technologies Group.

Sani-Tech Products, "Sani-Flo/STHT—Silicone Tubing/Assemblies," Flexible Tubing, Hose and Assemblies, Product Selection and Design Guide, 1991, 11 pages, Sani-Tech, Inc.

Sani-Tech Products, "Sani-Link Unitized Fittings," 2 pages.

* cited by examiner

STERILE PORT CONNECTION

CROSS-REFERENCE TO RELATED APPLICATION(S)

This application claims priority under 35 U.S.C. § 119(e) to U.S. Patent Application No. 62/149,162 entitled "STERILE PORT CONNECTION," by Michael R. Huschke, filed Apr. 17, 2015, which is assigned to the current assignee hereof and incorporated herein by reference in its entirety.

FIELD OF THE DISCLOSURE

The present disclosure relates to sterile connections, and more particularly to, sterile connections between a tubing and a port.

RELATED ART

The state of the art includes a variety of style of port connections, but all have drawbacks. For example, state of the art port connections in isolation bags require a double sided port and a first tubing coupled to the port outside of the bag and a separate tubing coupled to the port inside the bag. This double connection is time consuming and expensive to produce and provides unnecessary points of failure.

The present inventors have created a unique port connection assembly and methods of forming a sterile connection that overcomes these and other drawbacks. For example, embodiments of the present disclosure provide a single port aseptic connection where the bore of the port does not form a fluid facing surface.

BRIEF DESCRIPTION OF THE DRAWINGS

Embodiments are illustrated by way of example and are not limited in the accompanying figures.

Skilled artisans appreciate that elements in the figures are illustrated for simplicity and clarity and have not necessarily been drawn to scale. For example, the dimensions of some of the elements in the figures may be exaggerated relative to other elements to help to improve understanding of embodiments of the invention.

DETAILED DESCRIPTION

The following description in combination with the figures is provided to assist in understanding the teachings disclosed herein. The following discussion will focus on specific implementations and embodiments of the teachings. This focus is provided to assist in describing the teachings and should not be interpreted as a limitation on the scope or applicability of the teachings. However, other embodiments can be used based on the teachings as disclosed in this application.

As used herein, the phrase "engagement element" refers to a feature disposed on an outer surface or on an inner diameter of the port, such as in bore of the port, that is adapted to engage with a separate element from the port. An engagement element can include protrusions, such as a barb, depressions, recesses, or any other structure that is adapted to engage with a separate element from the port when making a sterile connection.

As used herein, a "vessel" refers to any structure capable of receiving and a holding a fluid, which could include liquids, gases, or combinations thereof. A vessel includes, but is not limited to an open vessel, a closed vessel, a rigid vessel, a flexible vessel, a transparent vessel, a bag such as a mixing bag or an isolation bag, a drum, a container, a room, or any other structure to which a sterile connection is desired.

The terms "comprises," "comprising," "includes," "including," "has," "having" or any other variation thereof, are intended to cover a non-exclusive inclusion. For example, a method, article, or apparatus that comprises a list of features is not necessarily limited only to those features but may include other features not expressly listed or inherent to such method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

Also, the use of "a" or "an" is employed to describe elements and components described herein. This is done merely for convenience and to give a general sense of the scope of the invention. This description should be read to include one, at least one, or the singular as also including the plural, or vice versa, unless it is clear that it is meant otherwise. For example, when a single item is described herein, more than one item may be used in place of a single item. Similarly, where more than one item is described herein, a single item may be substituted for that more than one item.

Unless otherwise defined, all technical and scientific terms used herein have the same meaning as commonly understood by one of ordinary skill in the art to which this invention belongs. The materials, methods, and examples are illustrative only and not intended to be limiting. To the extent not described herein, many details regarding specific materials and processing acts are conventional and may be found in textbooks and other sources within the fluid transfer arts.

The present disclosure is directed to sterile seamless port connections. The concepts are better understood in view of the embodiments described below that illustrate and do not limit the scope of the present invention.

Figure 1:
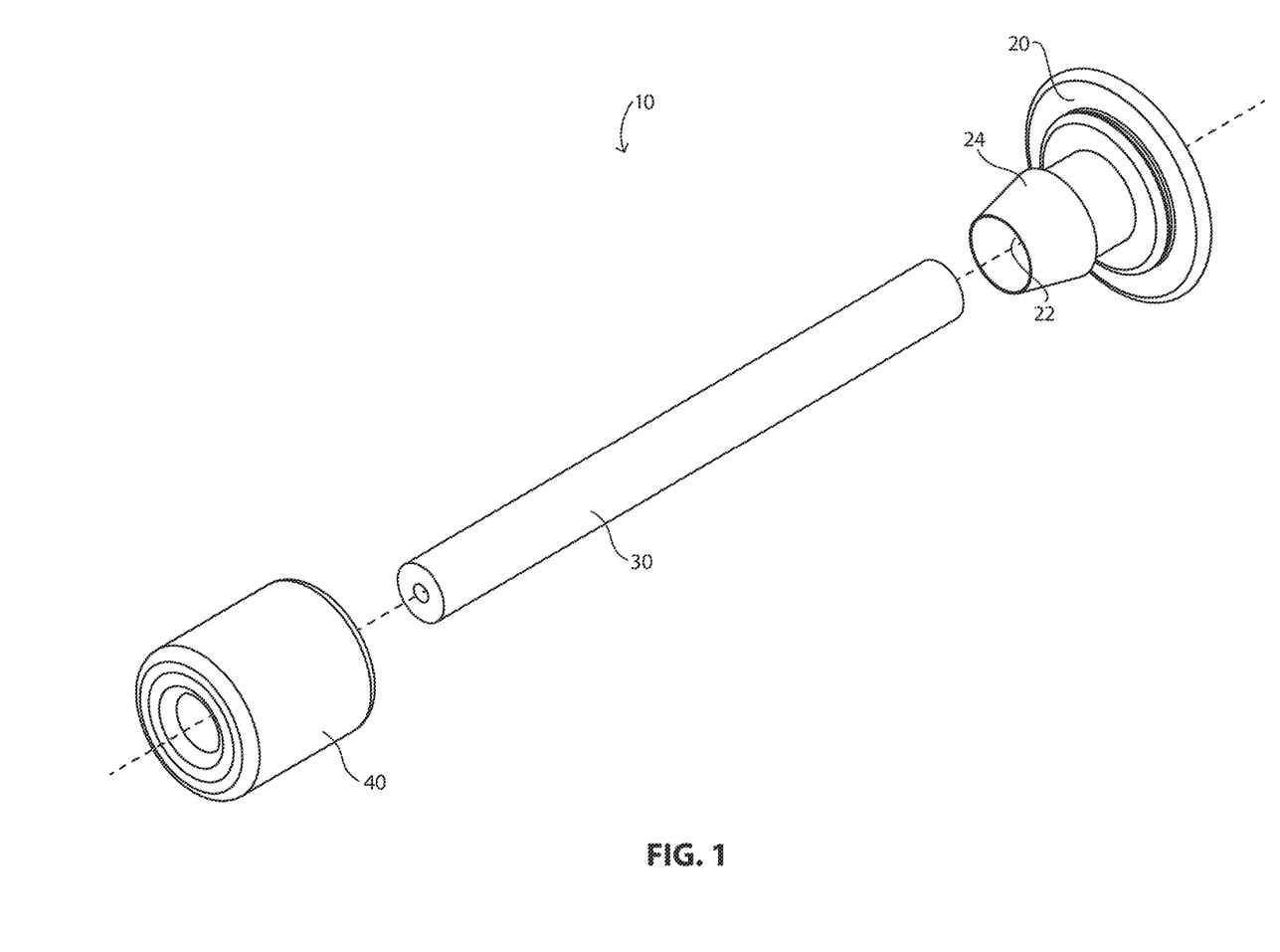
FIG. 1 illustrates an exploded perspective view of a connection assembly according to one embodiment.
Figure 2:
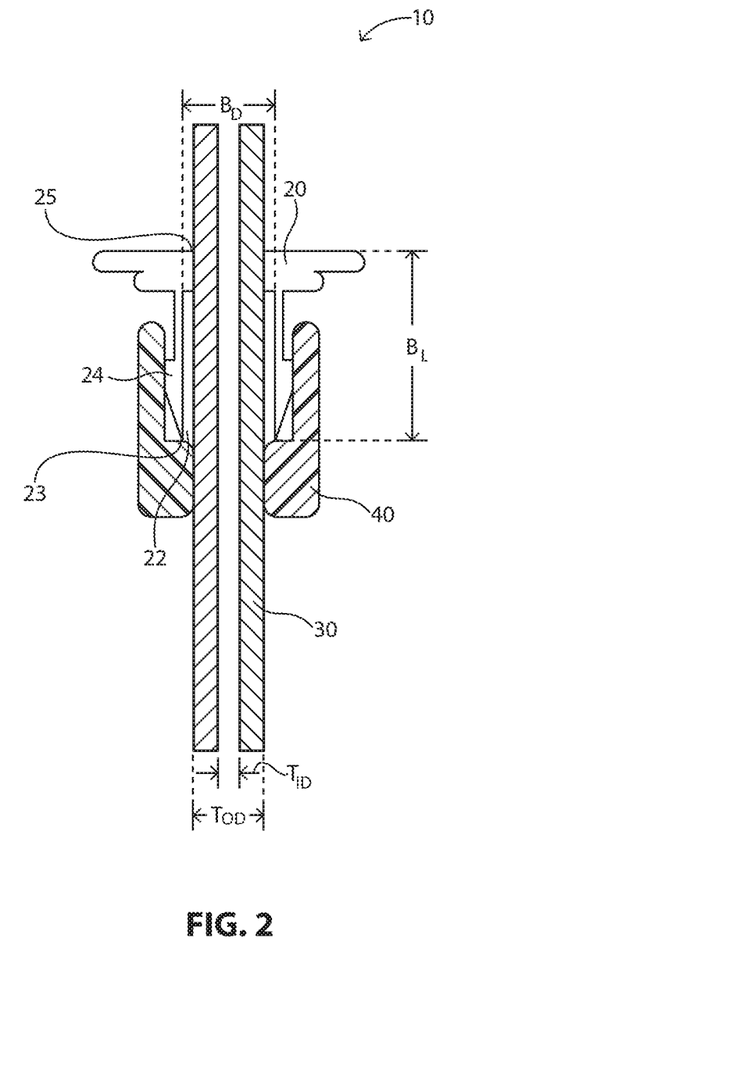
FIG. 2 illustrates a cross-section view of the assembled connection assembly of FIG. 1.

Referring now to FIGS. 1 and 2, one embodiment of a sterile connection 10 includes a port 20 having a bore 22 defining a passageway; and a tube 30 disposed within the bore 22 of the port 20. An overmolded element 40 couples the tube 30 to the port 20.

As illustrated in FIGS. 1 and 2, in particular embodiments, the port 20 can include one or more engagement elements 24 disposed on the outer surface of the port 20. For example, the one or more engagement elements 24 can include protrusions such as barbs, depressions, recesses, or any combination thereof. In very particular embodiments, the one or more engagement elements 24 can include one or more barbs.

As illustrated in FIG. 1, the one or more engagement elements 24 can be continuously disposed about the outer circumference of the port 20. In other embodiments, the one or more engagement elements can be discontinuously disposed about the outer circumference of the port.

In certain embodiments, the one or more engagement elements 24 can include at least 2 or even at least 3 distinct engagement elements 24.

Referring again to FIGS. 1 and 2, the port 20 can include a bore 22 that defines a passageway through the port 20. The bore 22 has a diameter $B_D$ and has a length $B_L$ extending axially from the distal end 23 of the bore 22 to the proximal end 25 of the bore 22.

In particular embodiments, the diameter $B_D$ of the bore 22 can be generally consistent through the length $B_L$ of the bore 22. In other embodiments, the bore 22 can include a taper, such as a taper from the distal end 23 to the proximal end 25. In still further embodiments, the bore can include a taper from the proximal end 25 to the distal end 23.

In certain embodiments, the tube 30 can extend entirely through the bore 22, such that the bore 22 does not form a fluid facing surface in a formed connection. In other embodiments, the tube 30 can extend partially within the bore.

In certain embodiments, after insertion of the tube 30 through the bore 22, a fitting 50 (see FIG. 6) can be attached to the tube 30. For example, a fitting 50 can include a sampling device, such as a syringe; a connector, such as a tee, a wye, a cross; or a valve or any other structure to which it may be advantages to couple the end of the tube.

Figure 6:
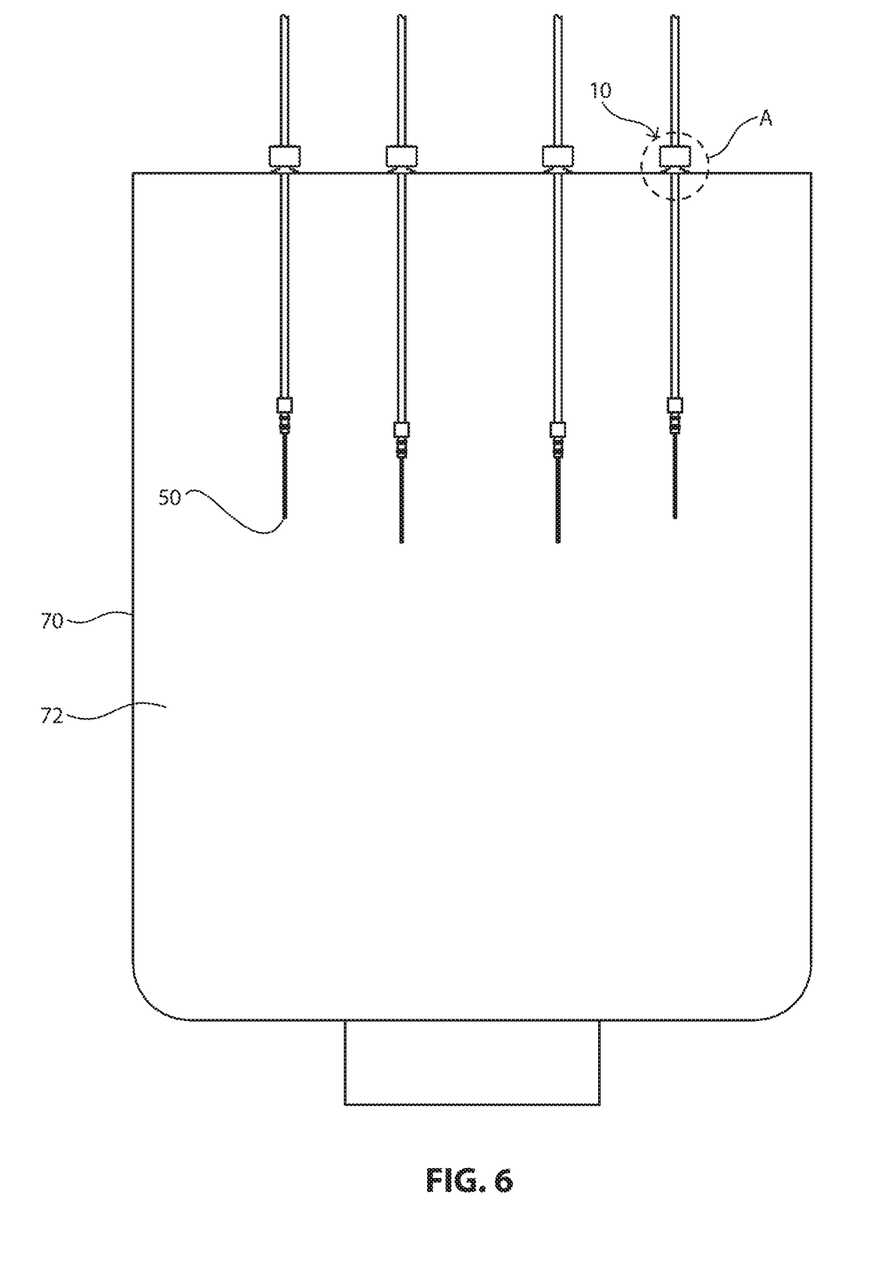
FIG. 6 illustrates a perspective view of a connection assembly coupled to a vessel according to one embodiment.

For example, as illustrated in FIG. 6, the tube 30 can be coupled to a sampling device fitting 50, such as a syringe after insertion of the tube 30 through the bore 22 of the port 20.

Referring again to FIG. 2, the tube 30 can have an outside diameter $T_{OD}$ that is generally the same as or less than the diameter of the bore. In fact, a particular advantage of certain embodiments of the present disclosure is the ability to use multiple tube sizes with a single port and still obtain an aseptic connection. For example, since the overmolded element is formed directly on the tube and port after insertion of the tube through the bore, any tube having an outer diameter that is generally equal to or less than the bore diameter can be aseptically connected.

Accordingly, in certain embodiments, the tube 30 can directly contact the surface of the bore 22. In other embodiments, the outer profile of the tube 30 can be spaced apart from the surface of the bore 22. In still further embodiments, the outer profile of the tube can be complementary to the profile of the bore, as viewed in the cross-section.

In certain embodiments, the inside profile of the tube and/or the bore can have a generally concentric profile.

Referring to FIGS. 1 to 4, the sterile connection 10 can include an overmolded element 40 coupling the tube 30 and port 20. The overmolded element 40 can be formed after insertion of the tube 30 within the bore 22 of the port 20. Overmolding can allow for a complimentary profile and intimate contact with the port 20 and the tube 30. Accordingly, in particular embodiments, the overmolded element 40 can be in intimate and direct contact with the outer surface of the tube 30 and the outer surface of the port 20.

In particular embodiments, the overmolded element 40 can be disposed about the one or more engagement elements 24 disposed on the outer surface of the port 20. As described above, the overmolded element 40 can be in intimate contact with at least one of the one more engagement elements 24. In particular embodiments, the overmolded element 40 can be in intimate contact with at least two engagement elements 24.

The materials composing the tube 30, port 20, and overmolded element 40 can be selected depending on the particular application and according to various embodiments of the present disclosure.

In certain embodiments, the port 20 can be composed of a thermoplastic based material. For example, the port 20 can be composed of a polypropylene (PP) based material, a polyethylene (PE) based material, such as a high density polyethylene (HDPE) based material or a low density polyethylene (LDPE), a fluoropolymer based material, such as PFA or PVDF, a polyamide based material, such as Nylon; or any combination thereof. In particular embodiments, the port 20 can be composed of a polypropylene (PP) based material, a polyethylene (PE) based material, such as a high density polyethylene (HDPE) based material or a low density polyethylene (LDPE), or combinations thereof.

A particular advantage of certain embodiments of the present disclosure is a wide diversity of possible materials for formation of the port. For example, as described above, certain embodiments of the sterile connection include the tube extending entirely through the bore of the port such that the port does not form a fluid facing surface. In such embodiments, since the port is non-fluid facing, the materials composing the port do not have to satisfy the stringent requirements of fluid contacting surface, particularly in the biopharmaceutical field that involves very sensitive fluids.

In further embodiments, the tube 30 can be composed of a thermoset based material. For example, the tube 30 can be composed of a silicone based material.

In certain embodiments, the tube 30 can be composed of a thermoplastic material. For example, in particular embodiments, the tube can be composed of a thermoplastic elastomer (TPE) based material, such as C-Flex®.

In certain embodiments, the overmolded element 40 can be composed of a thermoplastic based material. For example, the overmolded element 40 can be composed of a polypropylene (PP) based material, a polyvinyl (PV) based material, such as polyvinyl chloride (PVC) based material, a elastomeric based material, or any combination thereof.

In further embodiments, the overmolded element 40 can be composed of a thermoset based material. For example, the overmolded can be composed of a silicone 40 based material.

The particular selection of materials composing the tubing 30, port 20, and overmolded element 40 achieve different embodiments of the present disclosure. It is to be understood that any combination of materials for the tube, port, and overmolded elements described above are within the scope of certain embodiments of the present disclosure.

In particular embodiments, the tubing 30, port 20, and overmolded element 40 can be composed of a material that allows for covalent bonding between one or both of the tubing and the port to the overmolded element.

Figure 3:
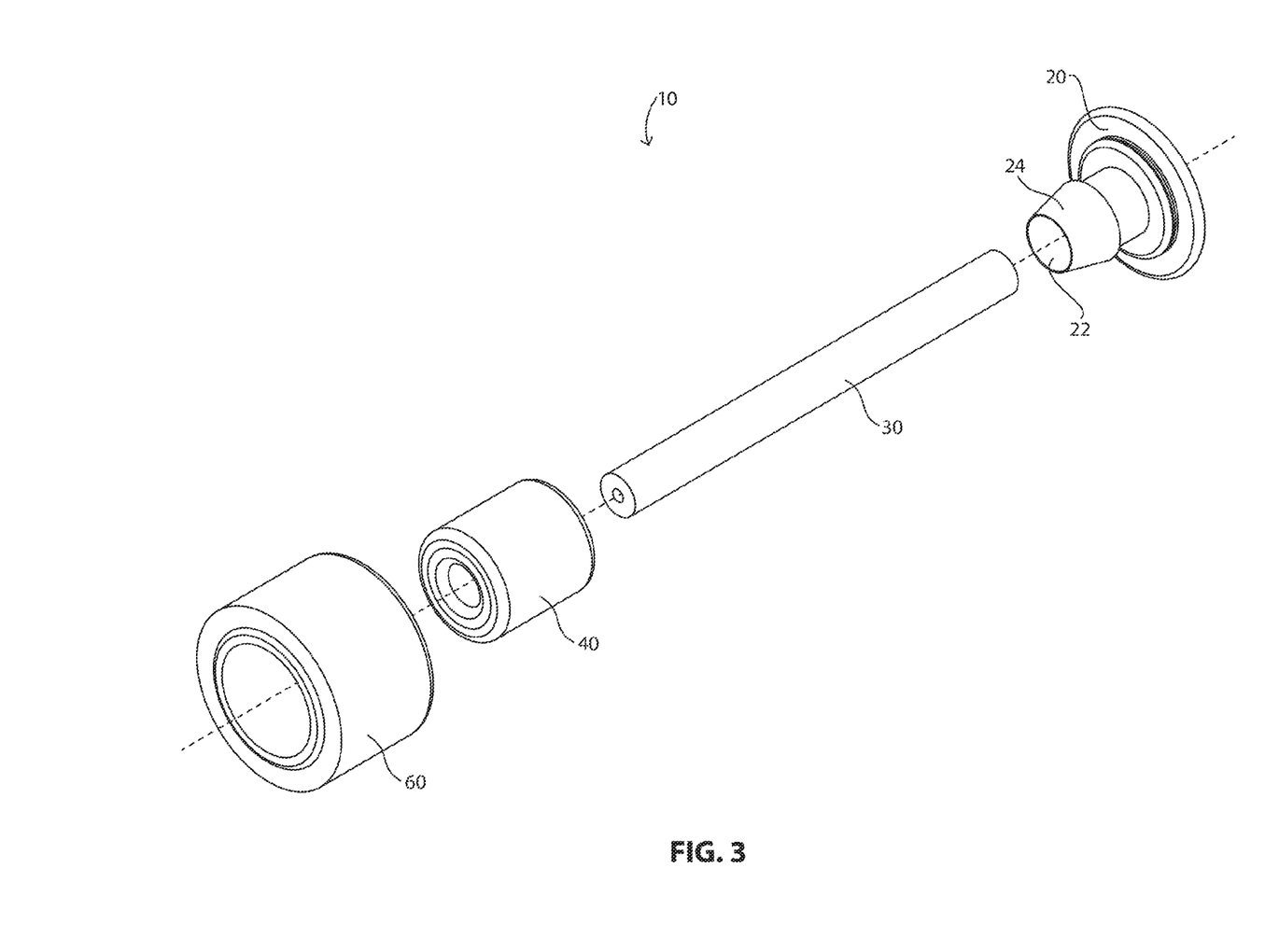
FIG. 3 illustrates an exploded perspective view of a connection assembly containing a compressive element according to another embodiment.
Figure 4:
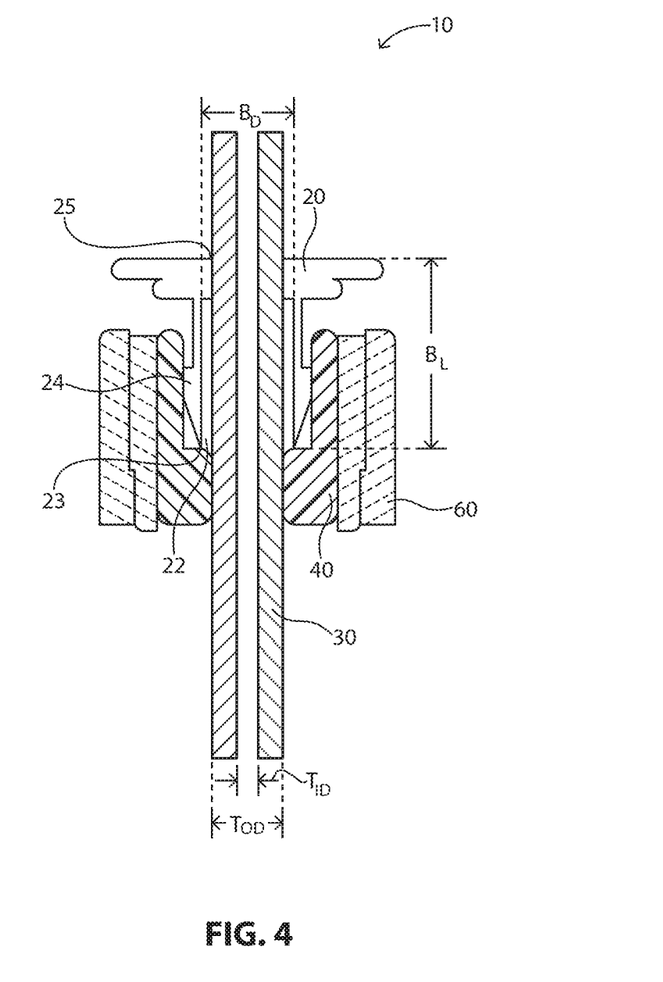
FIG. 4 illustrates a cross section view of the assembled connection assembly of FIG. 3.

In other embodiments, such as when covalent bonding between the one or both of the tubing 40 and the port 20 to the overmolded element is not possible, the sterile connection can further include a compressive element 60 as illustrated in FIGS. 3 and 4. The compressive element 60 can serve to provide a compressive force radially inwardly to secure the overmolded element about the port. For example, the compressive element 50 can be disposed over the port and the overmolded element about at least one of the one more engagement elements. A compressive element can include, for example, a clamp such as a Barblock® (available from Saint-Gobain Performance Plastics Corporation), a band, a zip-tie or any other structure adapted to provide a compressive force radially inwardly. Examples of suitable clamps can include those described in U.S. patent application Ser. No. 12/437,260, U.S. Pat. Nos. 7,922,213, 7,922,212, and U.S. patent application Ser. No. 10/963,457.

Figure 5:
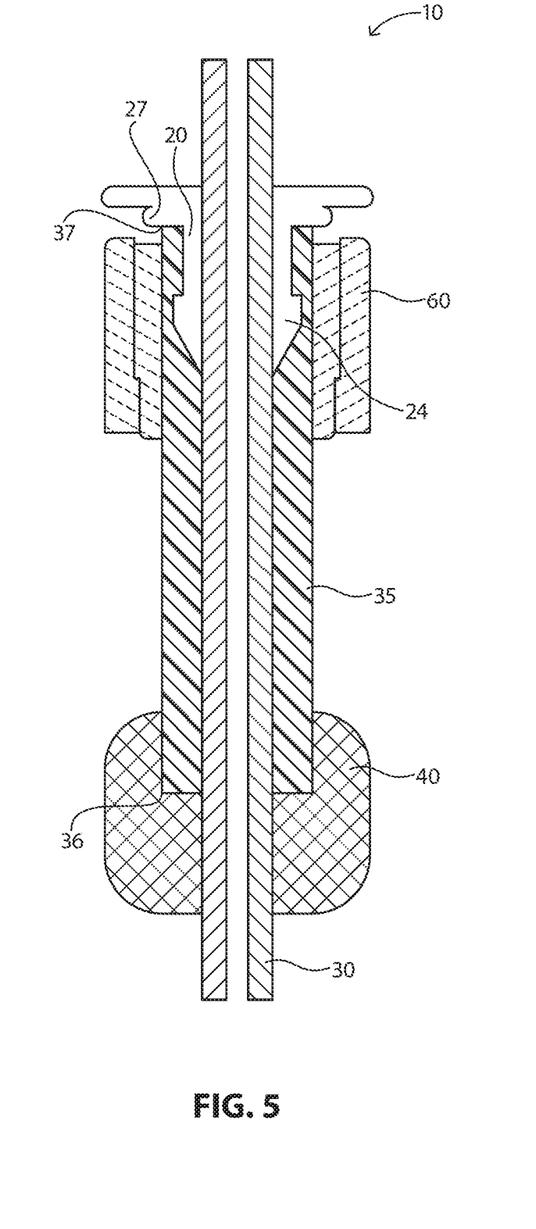
FIG. 5 illustrates a cross-section view of a connection assembly according to another embodiment.

Referring now to FIG. 5, one embodiment of a sterile connection 10 can include a first tube 30 disposed within the bore 22 of the port 20, a second tube 35 disposed over the first tube 30 and disposed over the port 20; an overmolded element 40 coupling the first tube 30 and the second tube 35 at a distal end 36 and a compressive element 60 disposed about the second tube 35 and the port 20. As illustrated in FIG. 5, the port 20 can include an engagement element 24, such as a barb, and the compressive element 40 can be disposed about the engagement element 24 and the second tube 35. Accordingly, the first and second tubes 30,35 are sealed together at the distal end 36 of the second tube 35 via the overmolded element 40, and the second tube 35 and the port 20 are sealed together by the compressive element 60 at the proximal end 37 of the second tube 35.

Figure 7:
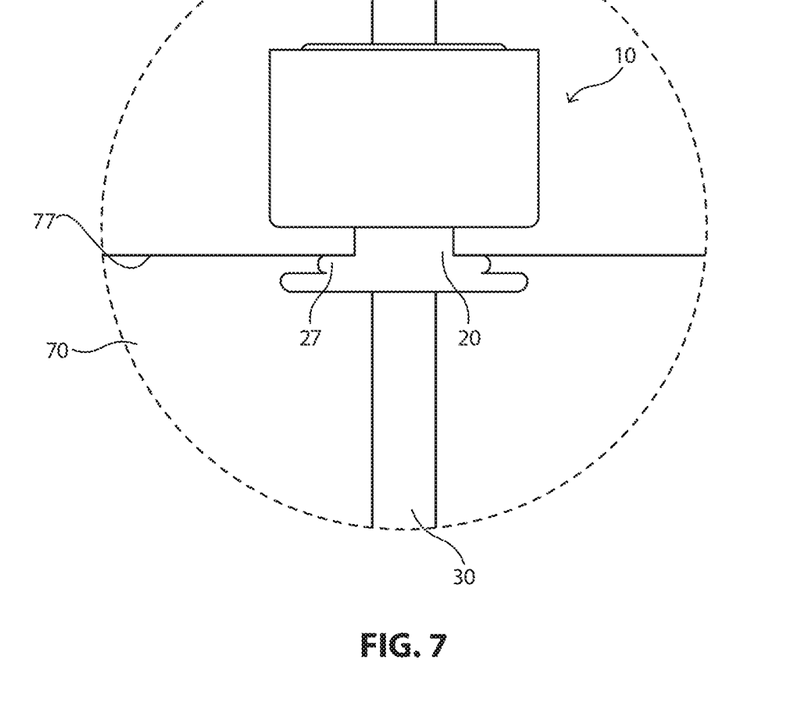
FIG. 7 illustrates a close-up view of callout A of FIG. 6.

Referring to FIGS. 6 and 7, another aspect of the present disclosure is directed to an assembly including any embodiment of the sterile connection 10 described herein and a vessel 70 having an interior cavity 72. The port 20 can be coupled to the vessel 70 and the bore 22 of the port 20 can be in fluid communication with the interior cavity 72 of the vessel 70. The tubing 30 can extend from outside of the vessel 70, through the port 20, and into the interior cavity 72 of the vessel 70. The tubing can the be sealed to the port as described in any of the embodiments provided above, such as, for example overmolding an overmolded element over the port and the tubing and optionally providing a compressive element.

In certain embodiments, the vessel 70 can include a flexible vessel that is coupled to the port 20. A flexible vessel refers to a vessel having at least one flexible sidewall.

In other embodiments, the vessel 70 can include a rigid vessel that is coupled to the port.

In still further embodiments, the assembly can include a flexible vessel 70 that is coupled to the port 20 and a rigid vessel (not shown) to support the flexible vessel 70 and including a structure that can accommodate the port 20 coupled to the flexible vessel 70. For example, the rigid vessel can include an aperture having a size large enough for the port to protrude through a wall of the rigid vessel.

As described above, in particular embodiments, the tubing 30 can extend entirely through the bore 22 of the port 20, and therefore open into the inner cavity 72 of the vessel 70. Accordingly, the bore 22 of the port 20 can be non-fluid facing.

The port 20 can be coupled to the vessel 70 by any desirable method. For example, in particular embodiments, the port 20 can be adhered, bonded, welded, or otherwise secured to the vessel 70. As a particular example and referring again to FIG. 7, the port 20 can include a flange 27 extending radially from the bore 22. The flange 27 can be welded to the inner or outer surface of the vessel. In particular embodiments, a hole is made in the vessel, and the port 20 is inserted through the hole such that the flange 27 contacts the inner surface 77 of the vessel 70 and is coupled thereto.

In very particular embodiments, the vessel 70 can be an isolation vessel, such as an isolation bag. An isolation vessel does not involve the direct fluid contact with the vessel, but rather provides an isolated environment to protect sensitive fluids. The interior cavity of the isolation bag must remain aseptic during use. Isolation bags are typically used in the pharmaceutical industry, such as to sample a given fluid and can include user manipulation ports such that a user can manipulate contents within the isolation bag without breaking the aseptic nature of the interior cavity. Traditional methods to connect a sampling device, such as a syringe port that is fluid communication with a structure outside of the isolation bag, included incorporating a double sided port, and making two connections, one wholly outside of the isolation bag, and one wholly inside the isolation bag. Accordingly, certain embodiments of the present disclosure as described above allow for the use of a singe port, with one connection where the tubing extends from outside of the isolation bag all the way through the port. The end of the tubing can then be connected to a fitting, such as a sampling device.

Many different aspects and embodiments are possible. Some of those aspects and embodiments are described below. After reading this specification, skilled artisans will appreciate that those aspects and embodiments are only illustrative and do not limit the scope of the present invention. Embodiments may be in accordance with any one or more of the items as listed below.

Item 1. An assembly comprising:
a. a port comprising a bore defining a passageway;
b. a tube disposed through the bore; and
c. an overmolded element coupling the tube to the port;
d. wherein the bore is non-fluid facing.

Item 2. An assembly comprising:
a. a port comprising a bore defining a passageway;
b. a first tube disposed through the bore; and
c. a second tube disposed over the first tube and disposed over the port;
d. an overmolded element coupling the first tube to the second tube; and
e. a compressive element disposed over the second tube and the port.

Item 3. An assembly comprising:
a. a vessel having an interior cavity;
b. a port having a bore defining a passageway into the interior cavity of the vessel; and
c. a tube;
d. wherein the tube is coupled to the port;
e. wherein the tube extends into the inner cavity of the vessel; and
f. wherein the port is non-fluid facing.

Item 4. An assembly comprising:
a. an isolation vessel having an interior cavity;
b. a port coupled to the isolation vessel, wherein the port comprises a bore defining a passageway to the interior cavity of the vessel; and
c. a tube extending through the bore and coupled to the port, wherein the coupling between the port and the tubing is aseptic.

Item 5. An assembly comprising:
a. a port having a bore defining a passageway, the bore having an inner diameter;
b. a tube extending through the bore, the tube having an outer diameter, wherein the outer diameter of the tube is less than the inner diameter of the bore;
c. an overmolded element disposed over and coupling the tube and port.

Item 6. An assembly comprising:
a. a first component having a bore defining a passageway;
b. a second component having a bore defining a passageway and comprising at least one engagement element disposed on an outer surface of the second component, wherein the inner diameter of the second component is generally equal to or greater than the outside diameter of the first component, wherein the first component is disposed within the bore of the second component, and an overmolded element coupling the first component to the second component.

Item 7. The assembly of item 6, wherein the first component comprises a tube; and wherein the second component comprises a port.

Item 8. A method of making a connection between a tubing and a port, the method comprising:
 a. providing a port comprising a bore defining a passageway and one or more engagement elements disposed about an outer periphery of the port;
 b. inserting a tube through bore of the port; and
 c. overmolding an element about the engagement elements and the tube.

Item 9. A method of making a connection between a tubing and a port, the method comprising:
 a. providing a port comprising a bore defining a passageway and one or more engagement elements disposed about an outer periphery of the port;
 b. inserting a first tube through bore of the port;
 c. disposing a second tube over the first tube and about one or more of the engagement elements on the port; and
 d. overmolding an element to couple the first tube to the second tube; and
 e. providing a compressive element to provide radial compression of the second tube about the one or more engagement elements of the port.

Item 10. The assembly or method of any one of the preceding items, wherein the port further includes one or more engagement elements disposed about an outer periphery of the port; the tube is composed of a silicone based material; and the overmolded element is composed of a silicone based material; and wherein the assembly further comprises a retention element disposed about and retaining the overmolded element about the port.

Item 11. The assembly or method of any one of the preceding items, wherein the port further includes one or more engagement elements disposed about an outer periphery of the port; the tube is composed of a thermoplastic based material; and the overmolded element is composed of a thermoplastic based material; wherein the overmolded element is covalently bonded to the tube.

Item 12. The assembly or method of any one of the preceding items, wherein the bore of the port is non-fluid facing.

Item 13. The assembly or method of any one of the preceding items, wherein the port is non-fluid facing.

Item 14. The assembly or method of any one of the preceding items, wherein the port is entirely non-fluid facing.

Item 15. The assembly or method of any one of the preceding items, wherein the port further includes one or more engagement elements disposed about an outer periphery of the port.

Item 16. The assembly or method of any one of the preceding items, wherein the one or more engagement elements comprise a barb.

Item 17. The assembly or method of any one of the preceding items, wherein the port does not form a fluid contacting surface.

Item 18. The assembly or method of any one of the preceding items, wherein the port is composed of a thermoplastic based material.

Item 19. The assembly or method of any one of the preceding items, wherein the port is composed of a polypropylene (PP) based material, a polyethylene based material, such as a high density polyethylene (HDPE) based material or a low density polyethylene (LDPE), a fluoropolymer based material, such as PFA or PVDF, a polyamide based material, such as Nylon; or any combination thereof.

Item 20. The assembly or method of any one of the preceding items, wherein the port is composed of a polypropylene (PP) based material, high density polyethylene (HDPE) based material, a low density polyethylene (LDPE), a fluoropolymer based material or combinations thereof.

Item 21. The assembly or method of any one of the preceding items, wherein the assembly or method further comprises a vessel having an interior cavity, wherein the port is disposed on the vessel, and wherein the bore defines a passageway into the interior cavity of the vessel.

Item 22. The assembly or method of any one of the preceding items, wherein the vessel comprises at least one flexible wall.

Item 23. The assembly or method of any one of the preceding items, wherein the vessel comprises a flexible bag.

Item 24. The assembly or method of any one of the preceding items, further comprising a rigid vessel and a flexible vessel.

Item 25. The assembly or method of any one of the preceding items, wherein the vessel comprises an isolation bag.

Item 26. The assembly or method of any one of the preceding items, wherein the overmolded element is composed of a thermoplastic based material.

Item 27. The assembly or method of any one of the preceding items, wherein the overmolded element is composed of a thermoplastic elastomer based material.

Item 28. The assembly or method of any one of the preceding items, wherein the overmolded element is composed of a silicone based material.

Item 29. The assembly or method of any one of the preceding items, wherein the overmolded element is composed of a polypropylene based material, a polyvinyl based material, such as polyvinyl chloride (PVC) based material, a thermoplastic elastomeric based material, or any combination thereof.

Item 30. The assembly or method of any one of the preceding items, wherein the tube is composed of a thermoplastic based material.

Item 31. The assembly or method of any one of the preceding items, wherein the tube is composed of a thermoplastic elastomer based material.

Item 32. The assembly or method of any one of the preceding items, wherein the tube is composed of a silicone based material.

Item 33. The assembly or method of any one of the preceding items, wherein the compressive element applies a compressive force to squeeze the overmolded element or second tube about at least one of the one or more engagement elements.

Item 34. The assembly or method of any one of the preceding items, wherein the compressive element comprises a clamp such as a barblock, a band, or a zip-tie.

Item 35. The assembly or method of any one of the preceding items, wherein the compressive element comprises a barblock.

Item 36. The assembly or method of any one of the preceding items, wherein the outside diameter of the tube is generally the same as or less than the inner diameter of the bore.

Item 37. The assembly or method of any one of the preceding items, wherein the outside diameter of the tube is generally the same as the inner diameter of the bore.

Item 38. The assembly or method of any one of the preceding items, wherein the tubing extends entirely through the port.

Item 39. The assembly or method of any one of the preceding items, wherein the tubing extends entirely through the port and opens into the inner cavity of the vessel.

Item 40. The assembly or method of any one of the preceding items, wherein the outer surface of the tube directly contacts the inner surface of the bore.

Item 41. The assembly or method of any one of the preceding items, wherein the outer surface of the tube is spaced apart from the inner surface of the bore.

Item 42. The assembly or method of any one of the preceding items, wherein the outer profile of the tube is complementary to an inner profile of the bore as viewed in the cross-section.

Item 43. The assembly or method of any one of the preceding items, wherein the outer profile of the tube and the inner profile of the bore are generally circular as viewed in the cross-section.

Item 44. The assembly or method of any one of the preceding items, wherein the port is coupled to a wall of the vessel.

Item 45. The assembly or method of any one of the preceding items, wherein the port is coupled to a flexible wall of the vessel.

Item 46. The assembly or method of any one of the preceding items, wherein the port is coupled to an interior surface of the vessel.

Item 47. The assembly or method of any one of the preceding items, wherein the assembly further comprises a fitting disposed on the end of the tubing.

Item 48. The assembly or method of any one of the preceding items, wherein the fitting comprises a sampling device.

Item 49. The assembly or method of any one of the preceding items, wherein the fitting comprises a syringe.

Note that not all of the activities described above in the general description or the examples are required, that a portion of a specific activity may not be required, and that one or more further activities may be performed in addition to those described. Still further, the order in which activities are listed is not necessarily the order in which they are performed.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

The specification and illustrations of the embodiments described herein are intended to provide a general understanding of the structure of the various embodiments. The specification and illustrations are not intended to serve as an exhaustive and comprehensive description of all of the elements and features of apparatus and systems that use the structures or methods described herein. Separate embodiments may also be provided in combination in a single embodiment, and conversely, various features that are, for brevity, described in the context of a single embodiment, may also be provided separately or in any subcombination. Further, reference to values stated in ranges includes each and every value within that range. Many other embodiments may be apparent to skilled artisans only after reading this specification. Other embodiments may be used and derived from the disclosure, such that a structural substitution, logical substitution, or another change may be made without departing from the scope of the disclosure. Accordingly, the disclosure is to be regarded as illustrative rather than restrictive.

What is claimed is:

1. An assembly comprising:
   a. a port comprising a bore defining a passageway, and one or more engagement elements disposed about an outer periphery of the port;
   b. a tube disposed through the bore; and
   c. an overmolded element coupling the tube to the port;
   d. wherein the bore is non-fluid facing, wherein the one or more engagement elements comprises a barb.

2. The assembly of claim 1, wherein the port further includes one or more engagement elements disposed about an outer periphery of the port; the tube is composed of a silicone based material; and the overmolded element is composed of a silicone based material; and wherein the assembly further comprises a retention element disposed about and retaining the overmolded element about the port.

3. The assembly of claim 2, wherein the compressive element applies a compressive force to squeeze the overmolded element or second tube about at least one of the one or more engagement elements.

4. The assembly of claim 1, wherein the port further includes one or more engagement elements disposed about an outer periphery of the port; the tube is composed of a thermoplastic based material; and the overmolded element is composed of a thermoplastic based material; wherein the overmolded element is covalently bonded to the tube.

5. The assembly of claim 1, wherein the port is composed of a thermoplastic based material.

6. The assembly of claim 1, wherein the port is composed of a polypropylene (PP) based material, a polyethylene based material, a fluoropolymer based material, a polyamide based material, or any combination thereof.

7. The assembly of claim 1, wherein the overmolded element is composed of a thermoplastic based material.

8. The assembly of claim 1, wherein the overmolded element is composed of a silicone based material.

9. The assembly of claim 1, wherein the overmolded element is composed of a polypropylene based material, a polyvinyl based material, a thermoplastic elastomeric based material, or any combination thereof.

10. The assembly of claim 1, wherein the tube is composed of a thermoplastic based material.

11. The assembly of claim 1, wherein the tube is composed of a silicone based material.

12. The assembly of claim 1, wherein the outside diameter of the tube is generally the same as or less than the inner diameter of the bore.

13. The assembly of claim 1, wherein the assembly further comprises a fitting disposed on the end of the tube.

14. An assembly comprising:
   a. a port comprising a bore defining a passageway, and one or more engagement elements disposed about an outer periphery of the port;
   b. a first tube disposed through the bore; and
   c. a second tube disposed over the first tube and disposed over the port;

d. an overmolded element coupling the first tube to the second tube; and
e. a compressive element disposed over the second tube and the port, wherein the one or more engagement elements comprises a barb.

15. An assembly comprising:
a. a vessel having an interior cavity;
b. a port having a bore defining a passageway into the interior cavity of the vessel, and one or more engagement elements disposed about an outer periphery of the port; and
c. a tube;
d. wherein the tube is coupled to the port;
e. wherein the tube extends into the inner cavity of the vessel; and
f. wherein the port is non-fluid facing, wherein the one or more engagement elements comprises a barb, wherein the vessel comprises a flexible bag.

16. The assembly of claim 15, wherein the vessel comprises at least one flexible wall.

17. The assembly of claim 15, wherein the vessel comprises an isolation bag.

\* \* \* \* \*